US007323164B2

(12) United States Patent
Chandrasekher et al.

(10) Patent No.: US 7,323,164 B2
(45) Date of Patent: Jan. 29, 2008

(54) USE OF INTERLEUKIN-24 TO TREAT OVARIAN CANCER

(75) Inventors: Yasmin A. Chandrasekher, Mercer Island, WA (US); Patricia A. McKernan, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 35 days.

(21) Appl. No.: 10/410,447

(22) Filed: Apr. 8, 2003

(65) Prior Publication Data

US 2003/0215388 A1 Nov. 20, 2003

Related U.S. Application Data

(60) Provisional application No. 60/371,700, filed on Apr. 11, 2002.

(51) Int. Cl.
*A61K 45/00* (2006.01)
*A61K 38/21* (2006.01)
*C07K 14/54* (2006.01)

(52) U.S. Cl. .................. 424/85.2; 424/85.1; 514/12; 530/351

(58) Field of Classification Search .............. 435/7.2, 435/7.1; 424/85.2, 85.1; 514/12, 843
See application file for complete search history.

(56) References Cited

U.S. PATENT DOCUMENTS

| 4,603,044 | A | 7/1986 | Geho et al. ............... 424/9 |
| 5,252,714 | A | 10/1993 | Harris et al. ............. 530/391.9 |
| 5,382,657 | A | 1/1995 | Karasiewicz et al. ....... 530/351 |
| 5,738,846 | A | 4/1998 | Greenwald et al. ........ 424/85.7 |

FOREIGN PATENT DOCUMENTS

| WO | 95/11986 | 5/1995 |
| WO | 98/28425 | 7/1998 |
| WO | 98/46638 | 10/1998 |
| WO | WO 02/45737 | 6/2002 |
| WO | 03/016499 | 2/2003 |
| WO | 03/029262 | 4/2003 |
| WO | 03/075952 | 9/2003 |
| WO | 03/082255 | 10/2003 |
| WO | 03/087308 | 10/2003 |

OTHER PUBLICATIONS

Su et al. A combinatorial approach for selectively inducing programmed cell death in human pancreatic cancer cells. PNAS, Vo 98, No. 18, pp. 10332-10337, Aug. 2001.*
Ramesh et al, Cancer Research, Aug. 2003. vol. 63, pp. 5105-5113.*
Sieger et al Molecular therapy, Mar. 2004, vol. 9, No. 3, pp. 355-367.*
Frigerio et al., 1995, (GenBank Acc. No. T24746).
Washington University School of Medicine, 1995, (GenBank Acc. No. N23949).
Washington University School of Medicine, 1995, (GenBank Acc. No. N31850).
National Cancer Institute, 1997, (GenBank Acc. No. AA281696).
National Cancer Institute, 1997, (GenBank Acc. No. AA281635).
The Institute for Genomic Research, 1995, (GenBank Acc. No. AA370517).
The Institute for Genomic Research, 1995, (GenBank Acc. No. AA370518).
The Institute for Genomic Research, 1995, (GenBank Acc. No. AA344685).
The Institute for Genomic Research. 1995, (GenBank Acc. No. AA344685).
EST985910, 1997.
Sequence from Incyte Pharmaceuticals, Inc., (No. INC1261863), 1997.
Columbia University, 1994, (Acc. No. U16261.
EST1011900, Oct. 10, 1997.
Su et al., "Melanoma differentiation associated gene-7, *mda*-7/IL-24, selectively induces growth suppression, apoptosis and radiosensitization in malignant gliomas in a *p53*-independent manner," *Oncogene* 22:1164-1180, 2003.
Saeki et al., "Inhibition of human lung cancer growth following adenovirus-mediated *mda-7* gene expression in vivo," *Oncogene* 21:4558-4566, 2002, issue No. 29, Jul. 2002.
Ekmekcioglu et al., "Negative Association of Melanoma Differentiation-associated Gene (*mda-7*) and Inducible Nitric Oxide Synthase (iNOS) in Human Melanoma: MDA-7 Regulates iNOS Expression in Melanoma Cells," *Molecular Cancer Therapeutics* 2:9-17, 2003.
Gopalkrishnan, "INGN-241 Introgen," *Current Opinion in Investigational Drugs* 3(12):1773-1777, 2002.
Sauane et al., "MDS-7/IL-24: novel cancer growth suppressing and apoptosis inducing cytokine," *Cytokine & Growth Factor Reviews* 14:35-51, 2003.
Sarkar et al., "*mda-7* (IL-24): Signaling and Functional Roles," *Bio Techniques* 33:S30-S39, 2002.
Garn et al., "IL-24 is Expressed by Rat and Human Macrophages," *Immunobiol.* 205:321-334, 2002.
Sarkar et al., "*mda-7* (IL-24) mediates selective apoptosis in human melanoma cells by inducing the coordinated overexpression of the GADD family of genes by means of p38 MAPK," *PNAS* 99(15):10054-10059, 2002.

(Continued)

*Primary Examiner*—Eileen B. O'Hara
*Assistant Examiner*—Fozia Hamud
(74) *Attorney, Agent, or Firm*—Shelby J. Walker; Aaron A. Schutzer

(57) ABSTRACT

The present invention relates to the anti-cancer activity of IL-24 polypeptide molecules. IL-24 is a cytokine involved in inflammatory processes and human disease. The present invention includes Use of IL-24 for decreasing proliferation of ovarian cancer cells, treating ovarian cancer, amongst other uses disclosed. IL-24 polypeptides can be administered alone, or can be fused to cytotoxic moieties, and can be administered in conjunction with radiation or chemotherapeutic agents.

9 Claims, No Drawings

OTHER PUBLICATIONS

Sauane et al., "Mda-7/IL-24 Induces Apoptosis of Diverse Cancer Cell Lines Through JAK/STAT-Independent Pathways," *J. Cell. Physiol.* 196:334-345, 2003.

Caudell et al., "The Protein Product of the Tumor Suppressor Gene, Melanoma Differentiation-Associated Gene 7. Exhibits Immunostimulatory Activity and Is Designated IL-24," *J. Immunol.* 6041-6046, 2002.

Parrish-Novak, et al., "Interleukins 19, 20, and 24 Signal through Two Distinct Receptor Complexes," *J. Biol. Chem.* 277(49):47517-47523, 2002.

Kotenko, "The family of IL-10-related cytokines and their receptors: related, but to what extent?." *Cytokine & Growth Factor Reviews* 13:223-240, 2002.

Lebedeva et al., "Bcl-2 and Bcl-xL differentially protect human prostate cancer cells from induction of apoptosis by melanoma differentiation associated gene-7, mda-7/IL-24," *Oncogene* 22:8758-8773, 2003.

Vandenbroeck et al., "The Conserved Helix C Region in the Superfamily of Interferon-γ/Interleukin-10-related Cytokines Corresponds to a High-affinity Binding Site for the HSP70 Chaperone DnaK," *J. Biol. Chem.* 277(29):25668-25676, 2002.

Collins, "Generation and intial analysis of more than 15, 000 full-length human and mouse cDNA sequences," *PNAS* 99(26):16899-16903, 2002.

Kamps et al., "Massive targeting of liposomes, surface-modified with anionized albumins, to hepatic endothelial cells," *Proc. Natl. Acad. Sci. USA* 94:11681-11685, 1997.

Chang et al., "Molecular Advances in Pretargeting Radioimmunotherapy with Bispecific Antibodies," *Mol. Can. Ther.* 1:553-563, 2002.

Jiang et al., "The melanoma differentiation associated gene mda-7 suppresses cancer cell growth," *Proc. Natl. Acad. Sci. USA* 93:9160-9165, 1996.

O'Reilly et al., "Angiostatis: A Novel Angiogenesis Inhibitor That Mediates the Suppression of Metastases by a Lewis Lung Carcinoma," *Cell* 79:315-328, 1994.

Rusciano et al., "Murine Models of Liver Metastasis," *Invasion Metastasis* 95(14):349-361, 1994.

Molpus et al., "Characterization of a Xenograft Model of Human Ovarian Carcinoma Which Prodces Intraperitoneal Carcinomatosis and Metastases in Mice," *Int. J. Cancer* 67:588-595, 1996.

Moreno-Merlo et al., "Association between tissue hypoxia and elevated non-protein sulphydryl concentrations in human cervical carcinoma xenografts," *British Journal of Cancer* 81(6):989-993, 1999.

Vukovic et al.,"Multiparameter Fluorescence Mapping of Nonprotein Sulfhydryl Status in Relation to Blood Vessels and Hypoxia in Cervical Carcinoma Xenografts," *Int. J. Radiation Oncology Biol. Phys.* 52(3):837-843, 2002.

Delgado et al.. "The Uses and Properties of PEG-Linked Proteins," *Critical Reviews in Therapeutic Drug Carrier Systems* 9(3,4):249-304, 1992.

Duncan et al., "Polymer Conjugates, Pharmacokinetic Considerations for Design and Development," *Clin. Pharmacokinet* 27(4):290-306, 1994.

Francis et al., "PEGylation of cytokines and other therapeutic proteins and peptides: the importance of biological optimization of coupling techniques," *International J. of Hematology* 68:1-18, 1998.

Monkarsh et al., "Positional Isomers of Monopegylated Interferon α-2a: Isolation, Characterization, and Biological Activity," *Analytical Biochemistry* 247:434-440, 1997.

Ranade and Hollinger, Drug Delivery Systems (CRC Press, 1996).

Bremer et al., "Protein Delivery with Infusion Pumps," in *Protein Delivery:Physical Systems*, Sanders and Hendren (eds.) pp. 239-254 (Plenum Press, 1997).

Yewey et al., "Delivery of Proteins from a Controlled Release Injectable Implant," *Protein Delivery:Physical Systems*, Sanders and Hendren (eds.), pp. 93-117 (Plenum Press, 1997).

Bakker-Woudenberg et al., "Liposomes as Carriers of Antimicrobial Agents or Immunomodulatory Agents in the Treatment of Infections," *Eur. J. Clin. Microbiol. Infect. Dis.* 1:61-67, 1993.

Ranade, "Site-Specific Drug Delivery Using Liposomes as Carriers," in *Drug Delivery Systems*, Ranade and Hollinger (eds.), pp. 3-24 (CRC Press, 1995).

Ostro et al., "Use of liposomes as injectable-drug delivery systems." *American J. of Hospital Pharmacy* 46:15761587, 1989.

Scherphof et al., "Uptake and Intracellular Processing of Targeted and Nontargeted Liposomes by Rat Kupffer Cells In Vivo and In Vitro," *Ann. N.Y. Acad. Sci.* 446:368-385,1985.

Claassen et al., "The Effect of Elimination of Macrophages on the Tissue Distribution of Liposomes Containing [$^3$H]Methotrexate," *Biochim. Biophys. Acta.* 802:428-434, 1984.

Allen et al., "Pharmacokinetics of stealth versus conventional liposomes: effect of dose," *Biochim. Biophys. Acta.* 1068:133-141, 1991.

Allen et al., "Subcutaneous administration of liposomes: a comparison with the intravenous and intraperitoneal routes of injection," *Biochim. Biophys. Acta.* 1150:9-16, 1993.

Kato et al., "Modification of Liposomes by Addition of HCO60. I. Targeting of Liposomes to Liver by Addition of HCO60 to Liposomes," *Biol. Pharm. Bull.* 16(10):960-964, 1993.

Shimizu et al., "Formulation of Liposomes with a Soybean-Derived Sterylglucoside Mixture and Cholesterol for Liver Targeting." *Boil. Pharm. Bull.* 20(8):881-886, 1997.

Kato et al., "Targeted Delivery of Peptides, Proteins, and genes by Receptor-Mediated Endocytosis," *Crit. Rev. Ther. Drug Carrier Syst.* 14(3):287-331, 1997.

Murahashi et al., "Hepatic Accumulation of Glutamic Acid Branched Neogalactosyllipid Modified Liposomes," *Biol. Pharm. Bull.* 20(3):259-266, 1997.

Wu et al., "Increased Liver Uptake of Liposomes and Improved Targeting Efficacy by Labeling With Asialofetuin in Rodents," *Hepatology* 27(3):772-778, 1998.

Harasym et al., "Clearance properties of liposomes involving conjugated proteins for targeting," *Adv. Drug Deliv. Rev.* 32:99-118, 1998.

Anderson et al., "Entrapment of Human Leukocyte Interferon in the Aqueous Interstices of Liposomes," *Infect. Immun.* 31(3):1099-1103, 1981.

Anderson et al., "Increased Local Antitumor effects of Interleukin 2 Liposomes in Mice with MCA-106 Sarcoma Pulmonary Metastases," *Cancer Res.* 50:1853-1856, 1990.

Cohen et al., "Lipid-alginate interactions render changes in phospholipid bilayer permeability," *Biochim. Biophys. Scta* 1063:95-102, 1991.

Wassef et al., "Complement-Dependent Phagocytosis of Liposomes by Macrophages," *Meth. Enzymol.* 149:124, 1987.

Gombotz et al., "Biodegradable Polymers for Protein and Peptide Drug Delivery," *Bioconjugate Chem.* 6:332-351, 1995.

Bartus et al., "Sustained Delivery of Proteins for Novel Therapeutic Products," *Science* 281:1161-1162, 1998.

Putney et al., "Improving protein therapeutics with sustained-release formulations," *Nature Biotechnology* 16:153-157, 1998.

Putney, "Encapsulation of proteins for improved delivery," *Curr. Opin. Chem. Biol.* 2:548-552, 1998.

Gref et al., "Poly(ethylene glycol)-Coated Nanospheres: Potential Carriers for Intravenous Drug Administration," *Pharm. Biotechnol.* 10:167-198, 1997.

Cunningham et al., "A Phase 1 Dose-Escalation Pharmacokinetic and Pharmacodynamic Study of INGN 241 (Ad-mda7) in Patients with Advanced Solid Tumors," Cancer Gene Therapy, S2 (Dec. 12-14, 2002).

Chada et al., "The Multifunctional mda-7 Gene Encodes both Tumor Suppressor and $T_H I$ Cytokine (IL-24) Activities," Cancer Gene Therapy, S3 (Dec. 12-14, 2002).

Ramesh et al, "MDA-7/IL-24 is a Novel Ligand that Regulates Angiogenesis via the IL-22 Receptor," Cancer Gene Therapy S3 (Dec. 12-14, 2002).

Mhashikar et al., "MDA-7 Negatively Regulates the Beta-Catenin and P13K Signaling Pathways in Breast and Lung Tumor Cells." Cancer Gene Therapy S6 (Dec. 12-14, 2002).

Tong et al., "Immune Activation by Ad-mda7 (INGN 241) Gene Transfer in Advanced Cancer Patients," Cancer Gene Therapy S37 (Dec. 12-14, 2002).

De Groot-Kruseman et al., *J. Interferon & Cytokine Research 22(Suppl. 1)*: S-97, Abstract P-2-1, 2002.

He et al., *J. Interferon & Cytokine Research 22(Suppl. 1)*: S-97, Abstract P-1-23, 2002.

Kunz et al., *J. Interferon & Cytokine Research 22(Suppl. 1)*: S-97-S-98, Abstract P-2-3, 2002.

Musso et al., *J. Interferon & Cytokine Research 22(Suppl. 1)*: S-98, Abstract P-2-4, 2002.

Pirhonen et al., *J. Interferon & Cytokine Research 22(Suppl. 1)*: S-98, Abstract, P-2-6, 2002.

Strengell et al., *J. Interferon & Cytokine Research 22(Suppl. 1)*: S-99, Abstract P-2-8, 2002.

Whitters et al., *J. Interferon & Cytokine Research 22(Suppl. 1)*: S-99-S-100, Abstract P-2-11, 2002.

Witek et al., *J. Interferon & Cytokine Research 22(Suppl. 1)*: S-100, Abstract P-2-12, 2002.

* cited by examiner

SEQUENCE LISTING

<160> NUMBER OF SEQ ID NOS: 2

<210> SEQ ID NO 1
<211> LENGTH: 1762
<212> TYPE: DNA
<213> ORGANISM: Homo sapiens
<220> FEATURE:
<221> NAME/KEY: CDS
<222> LOCATION: (349)...(885)

<400> SEQUENCE: 1

```
gaattcggca cgaggtgaaa tgacttccac ggctgggacg ggaaccttcc acccacagct      60
atgcctctga ttggtgaatg gtgaaggtgc ctgtctaact tttctgtaaa aagaaccagc     120
tgcctccagg cagccagccc tcaagcatca cttacaggac cagagggaca agacatgact     180
gtgatgagga gctgctttcg ccaatttaac accaagaaga attgaggctg cttgggagga     240
aggccaggag gaacacgaga ctgagagatg aattttcaac agaggctgca aagcctgtgg     300
actttagcca gacccttctg ccctcctttg ctggcgacag cctctcaa atg cag atg     357
                                                      Met Gln Met
                                                        1 gtt gtg ctc cct tgc ctg ggt ttt acc ctg ctt ctc tgg agc cag gta     405
Val Val Leu Pro Cys Leu Gly Phe Thr Leu Leu Leu Trp Ser Gln Val
    5                  10                  15 tca ggg gcc cag ggc caa gaa ttc cac ttt ggg ccc tgc caa gtg aag     453
Ser Gly Ala Gln Gly Gln Glu Phe His Phe Gly Pro Cys Gln Val Lys
 20                  25                  30                  35 ggg gtt gtt ccc cag aaa ctg tgg gaa gcc ttc tgg gct gtg aaa gac     501
Gly Val Val Pro Gln Lys Leu Trp Glu Ala Phe Trp Ala Val Lys Asp
```

```
                 40                   45                    50
act atg caa gct cag gat aac atc acg agt gcc cgg ctg ctg cag cag      549
Thr Met Gln Ala Gln Asp Asn Ile Thr Ser Ala Arg Leu Leu Gln Gln
             55                   60                   65 gag gtt ctg cag aac gtc tcg gat gct gag agc tgt tac ctt gtc cac      597
Glu Val Leu Gln Asn Val Ser Asp Ala Glu Ser Cys Tyr Leu Val His
         70                   75                   80 acc ctg ctg gag ttc tac ttg aaa act gtt ttc aaa aac cac cac aat      645
Thr Leu Leu Glu Phe Tyr Leu Lys Thr Val Phe Lys Asn His His Asn
     85                   90                   95 aga aca gtt gaa gtc agg act ctg aag tca ttc tct act ctg gcc aac      693
Arg Thr Val Glu Val Arg Thr Leu Lys Ser Phe Ser Thr Leu Ala Asn
100                  105                  110                  115 aac ttt gtt ctc atc gtg tca caa ctg caa ccc agt caa gaa aat gag      741
Asn Phe Val Leu Ile Val Ser Gln Leu Gln Pro Ser Gln Glu Asn Glu
                 120                  125                  130 atg ttt tcc atc aga gac agt gca cac agg cgg ttt ctg cta ttc cgg      789
Met Phe Ser Ile Arg Asp Ser Ala His Arg Arg Phe Leu Leu Phe Arg
             135                  140                  145 aga gca ttc aaa cag ttg gac gta gaa gca gct ctg acc aaa gcc ctt      837
Arg Ala Phe Lys Gln Leu Asp Val Glu Ala Ala Leu Thr Lys Ala Leu
         150                  155                  160 ggg gaa gtg gac att ctt ctg acc tgg atg cag aaa ttc tac aag ctc      885
Gly Glu Val Asp Ile Leu Leu Thr Trp Met Gln Lys Phe Tyr Lys Leu
     165                  170                  175 tgaatgtcta gaccaggacc tccctccccc tggcactggt tgttccctg tgtcatttca     945 aacagtctcc cttcctatgc tgttcactgg acacttcacg cccttggcca tgggtcccat   1005
tcttggccca ggattattgt caaagaagtc attctttaag cagcgccagt gacagtcagg   1065
gaaggtgcct ctggatgctg tgaagagtct acagagaaga ttcttgtatt tattacaact   1125
ctatttaatt aatgtcagta tttcaactga agttctattt atttgtgaga ctgtaagtta   1185
catgaaggca gcagaatatt gtgccccatg cttctttacc cctcacaatc cttgccacag   1245 tgtgggcag tggatgggtg cttagtaagt acttaataaa ctgtggtgct tttttttggcc   1305 tgtctttgga ttgttaaaaa acagagaggg atgcttggat gtaaaactga acttcagagc   1365
atgaaaatca cactgtcttc tgatatctgc agggacagag cattgggtg ggggtaaggt    1425 gcatctgttt gaaaagtaaa cgataaaatg tggattaaag tgcccagcac aaagcagatc   1485
ctcaataaac atttcatttc ccacccacac tcgccagctc accccatcat cccttttccct  1545 tggtgccctc cttttttttt tatcctagtc attcttccct aatcttccac ttgagtgtca   1605
agctgacctt gctgatggtg acattgcacc tggatgtact atccaatctg tgatgacatt   1665
ccctgctaat aaaagacaac ataactcaaa aaaaaaaaaa aaaaaaaaa aaaaaaaaa    1725 aaaaaaaaa aaaaaaaaa aaaaaactg cggccgc                              1762

<210> SEQ ID NO 2
<211> LENGTH: 179
<212> TYPE: PRT
<213> ORGANISM: Homo sapiens

<400> SEQUENCE: 2

Met Gln Met Val Val Leu Pro Cys Leu Gly Phe Thr Leu Leu Leu Trp
 1               5                  10                  15

Ser Gln Val Ser Gly Ala Gln Gly Gln Glu Phe His Phe Gly Pro Cys
             20                  25                  30

Gln Val Lys Gly Val Val Pro Gln Lys Leu Trp Glu Ala Phe Trp Ala
```

-continued

```
                35                  40                  45
Val Lys Asp Thr Met Gln Ala Gln Asp Asn Ile Thr Ser Ala Arg Leu
    50                  55                  60

Leu Gln Gln Glu Val Leu Gln Asn Val Ser Asp Ala Glu Ser Cys Tyr
65              70                  75                  80

Leu Val His Thr Leu Leu Glu Phe Tyr Leu Lys Thr Val Phe Lys Asn
                85                  90                  95

His His Asn Arg Thr Val Glu Val Arg Thr Leu Lys Ser Phe Ser Thr
            100                 105                 110

Leu Ala Asn Asn Phe Val Leu Ile Val Ser Gln Leu Gln Pro Ser Gln
            115                 120                 125

Glu Asn Glu Met Phe Ser Ile Arg Asp Ser Ala His Arg Arg Phe Leu
            130                 135                 140

Leu Phe Arg Arg Ala Phe Lys Gln Leu Asp Val Glu Ala Ala Leu Thr
145                 150                 155                 160

Lys Ala Leu Gly Glu Val Asp Ile Leu Leu Thr Trp Met Gln Lys Phe
                165                 170                 175

Tyr Lys Leu
```

USE OF INTERLEUKIN-24 TO TREAT OVARIAN CANCER

REFERENCE TO RELATED APPLICATIONS

The present application is related to U.S. Provisional Application Serial No. 60/371,700 filed Apr. 11, 2002. Under 35 U.S.C. § 19(e)(1), this application claims benefit of said Provisional Applications.

BACKGROUND OF THE INVENTION

Cancer of the ovary is the leading cause of death from gynecologic malignancies and the fourth common cause of cancer-related death among women. This is in spite of the fact that the occurrence of ovarian cancer is relatively rare. Only 1.5% of women develop the disease, and it is only the seventh most common cause of cancer in women.

Ovarian cancer can be divided into three sub-types depending on the cell type involved, namely, epithelial, stromal and germ cell tumors.

At least 80% of malignant ovarian tumors arise form the coelomic epithelium. The most common type is serous crystadenocarcinoma, which accounts for 75% of cases of epithelial ovarian cancer.

Most women (75%) present with advanced-stage disease, and most have vague, nonspecific symptoms, such as dyspepsia, bloating, early-satiety anorexia, gas pains and backache. The most common early finding is an adnexal mass, which is often solid, irregular, and fixed. A patient may be asymptomatic until the disease is advanced. Occasionally, a patient presents with severe abdominal pain secondary to torsion of the ovarian mass. Late in the course, pelvic pain, anemia, cachexia, and abdominal swelling due to ovarian enlargement or accumulation of ascitic fluid usually occur. Nodular implants noted on the rectovaginal examination suggest extensive pelvic malignant disease.

Stromal tumors constitute only a tenth of ovarian malignancies but account for most of the hormone-secreting tumors.

Germ cell tumors comprise less than 5 percent of ovarian malignancies, occur in young women, and have a higher incidence in African-American women than Caucasian women. Functional effects of germ cell or stromal tumors include hyperthyroidism, feminization, and virilization.

After surgery to remove the tumor chemotherapy is usually provided. The initial chemotherapeutic regimen is three to six courses of chemotherapy. Paclitaxel is combined with cisplatin or carboplatin. Other chemotherapeutic drugs include topotecan, hexamethylmelamine, ifosfamide, doxorubicin, bleomycin and etoposide. In spite of the regimens, the five-year survival rate of patients with stage II disease is only fifty to seventy percent and thirty to forty percent for patients with stage III disease.

Thus, there is a need for new therapeutics that can be used to treat ovarian cancer.

DESCRIPTION OF THE INVENTION

The present invention fills this need by administering interleukin-24 (IL-24) to a mammalian having ovarian cancer. The present invention also provides a method for inhibiting the growth of ovarian cancer cells by bringing IL-24 or fragments comprising helices A-D of IL-24, into contact with said cancerous ovarian cells. Interleukin-24 and fragments comprising helices A-D of IL-24 can be produced according to the method described in International Patent Application Publication No. WO 95/11986, and Jiang, H. et al., *Proc. Natl. Acad. Sci. USA* 93, 9160-9165 (1996). The polynucleotide sequence of IL-24 is shown in SEQ ID NO: 1 and corresponding amino acid sequence is shown in SEQ ID NO: 2; the mature secreted form of the IL-24 polypeptide is shown from amino acid number 22 (Ala) to 179 (Leu) of SEQ ID NO: 2.

The quantities of IL-24 for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include, intravenous, peritoneal, intramuscular, transdermal or administration into the lung or trachea in spray form by means or a nebulizer or atomizer. Pharmaceutically acceptable carriers will include water, saline, buffers to name just a few. Dosage ranges would ordinarily be expected from 1 µg to 1000 µg per kilogram of body weight per day. However, the doses may be higher or lower as can be determined by a medical doctor with ordinary skill in the art. Excipients and stabilizers can possible be added. These include glycine, histidine, glutamate, aspartate, sugars, sucrose, trehalose, galactose sorbitol, arginine, D-and/or L amino acids, sugar alcohols, lactose, maltose, threonine, lysine, methionine, isoleucine, a surface active agent such as TWEEN 80, TWEEN 20, polyethylene glycol (PEG) (particularly those PEGs having molecular weights between 1000 and 35000 Da), cetyl alcohol, polyvinylpyrrolidone, polyvinyl alcohol, lanolin alcohol and sorbitan. A reducing agent may be included, such as cysteine, N-acetyl-cysteine, and thioglycerol. For a complete discussion of drug formulations and dosage ranges see *Remington's Pharmaceutical Sciences*, 18th Ed., (Mack Publishing Co., Easton, Pa., 2496), and *Goodman and Gilman's: The Pharmacological Bases of Therapeutics*, 9th Ed. (Pergamon Press 2496).

In addition, as IL-24 is useful in treating ovarian or cervical-specific cancers, the anti-tumor and anti-proliferative activity and effect of IL-24 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly MS, et al. *Cell* 79: 315-328, 1994). C57BL6/J mice are treated with an experimental agent either through daily injection of recombinant protein, agonist or antagonist or a one-time injection of recombinant adenovirus. Three days following this treatment, $10^5$ to $10^6$ cells are implanted under the dorsal skin. Alternatively, the cells themselves may be infected with recombinant adenovirus, such as one expressing IL-24, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 mm$^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., IL-24, on the ability of the tumor to recruit vasculature and undergo metastasis can thus be assessed. In addition, aside from using adenovirus, the implanted cells can be transiently transfected with IL-24. Use of stable IL-24 transfectants as well as use of induceable promoters to activate IL-24 expression in vivo are known in the art and can be used in this system to assess IL-24 induction of metastasis. Moreover, purified IL-24 or IL-24-conditioned media can be directly injected in to this mouse model, and hence be used in this system. For general reference see, O'Reilly MS, et al. *Cell* 79:315-328, 1994; and Rusciano D, et al. Murine Models of Liver Metastasis. *Invasion Metastasis* 14:349-361, 1995.

Similarly, animal tumor models such as human xenograft models in immunocompromised animals are used for cervical and ovarian cancer models and are known in the art. For example, one ovarian carcinoma model is as follows: NIH:OVCAR-5 cells injected into Swiss nude mice, as disclosed in Molpus, KL et al, *Int. J. Cancer* 68:588-95 (1996), which characterizes a xenograft model of human ovarian carcinoma which produces intraperitoneal carcinomatosis and metastases in mice. For example, one cervical carcinoma model is as follows: Cervical carcinoma: ME180 and SiHa human cervical squamous cell carcinoma lines grown in SCID mice. See, Moreno-Merlo F et al, *Br. J. Cancer* 81:989-93 (1999) and Vukovic, V. et al, Int. J. *Radiat Oncol Biol Phys* 52:837-43 (2002).

Suitable detectable molecules may be directly or indirectly attached to the IL-24 polypeptide, and include radionuclides, enzymes, substrates, cofactors, inhibitors, fluorescent markers, chemiluminescent markers, magnetic particles and the like. Suitable cytotoxic molecules may be directly or indirectly attached to the polypeptide, and include bacterial or plant toxins (for instance, diphtheria, toxin, saporin, Pseudomonas exotoxin, ricin, abrin and the like), as well as therapeutic radionuclides, such as iodine-131, rhenium-188 or yttrium-90 (either directly attached to the polypeptide, or indirectly attached through means of a chelating moiety, for instance). Polypeptides may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide. For these purposes, biotin/streptavidin is an exemplary complementary/anticomplementary pair.

In addition, IL-24 polypeptide-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a cytokine (e.g., IL-24), a detectable molecule, a cytotoxic molecule or a complementary molecule to a cell or tissue type of interest, e.g., to ovarian or cervical tissue. In instances where the domain only fusion protein includes a complementary molecule, the anti-complementary molecule can be conjugated to a detectable or cytotoxic molecule. Such domain-complementary molecule fusion proteins thus represent a generic targeting carrier or vehicle for cell/tissue-specific delivery of generic anti-complementary-detectable/cytotoxic molecule conjugates.

In another embodiment, IL-24 cytokine fusion proteins can be used for in vivo killing of target tissues (for example, ovarian cancer, or cervical cancer, or leukemia, lymphoma, lung cancer, colon cancer, melanoma, pancreatic cancer, skin, blood and bone marrow cancers, or other cancers wherein IL-24 receptors are expressed) (See, generally, Chang, C. H. et al, *Mol Cancer Ther* 7:553-63(2002)). The described fusion proteins enable targeting of a cytokine to a desired site of action, thereby providing an elevated local concentration of cytokine. Suitable IL-24 polypeptides target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, if the IL-24 polypeptide targets tumor cells or cancerous tissues, such polypeptide may be conjugated with a radionuclide, and particularly with a beta-emitting radionuclide, to reduce restenosis (e.g., in vascular tissue). Such therapeutic approaches pose less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide described herein can be delivered intravenously, intraarterially or intraductally, or may be introduced locally at the intended site of action.

For pharmaceutical use, the IL-24 are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, the IL-24 may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of IL-24 is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The IL-24 can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

For pharmaceutical use, the IL-24 polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a IL-24 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of IL-24 is an amount sufficient to produce a clinically significant change in a cancer, cell growth or immune function.

The present invention also contemplates chemically modified IL-24 polypeptide is linked with a polymer. Illustrative IL-24 polypeptides are soluble polypeptides comprising a mature IL-24 polypeptide or a fragment of the IL-24 polypeptide comprising helices A-D of the polypeptide. Typically, the polymer is water soluble so that the IL-24 polypeptide conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714).

The polymer may be branched or unbranched. Moreover, a mixture of polymers can be used to produce IL-24 polypeptide conjugates.

IL-24 polypeptide conjugates used for therapy can comprise pharmaceutically acceptable water-soluble polymer moieties. Suitable water-soluble polymers include polyethylene glycol (PEG), monomethoxy-PEG, mono-(C1-C10) alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. An IL-24 polypeptide conjugate can also comprise a mixture of such water-soluble polymers.

One example of a IL-24 polypeptide conjugate comprises an IL-24 polypeptide moiety and a polyalkyl oxide moiety attached to the N-terminus of the IL-24 polypeptide moiety. PEG is one suitable polyalkyl oxide. As an illustration, IL-24 polypeptide can be modified with PEG, a process known as "PEGylation." PEGylation of IL-24 polypeptide can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharimacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, IL-24 polypeptide conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with an IL-24 polypeptide. An example of an activated PEG ester is PEG esterified to N-hydroxysuccinimide. As used herein, the term "acylation" includes the following types of linkages between IL-24 polypeptide and a water soluble polymer: amide, carbamate, urethane, and the like. Methods for preparing PEGylated IL-24 polypeptide by acylation will typically comprise the steps of (a) reacting a IL-24 polypeptide with PEG (such as a reactive ester of an aldehyde derivative of PEG) under conditions whereby one or more PEG groups attach to IL-24 polypeptide, and (b) obtaining the reaction product(s). Generally, the optimal reaction conditions for acylation reactions will be determined based upon known parameters and desired results. For example, the larger the ratio of PEG: IL-24 polypeptide, the greater the percentage of polyPEGylated IL-24 polypeptide product.

The product of PEGylation by acylation is typically a polyPEGylated IL-24 polypeptide product, wherein the lysine ε-amino groups are PEGylated via an acyl linking group. An example of a connecting linkage is an amide. Typically, the resulting IL-24 polypeptide will be at least 95% mono-, di-, or tri-pegylated, although some species with higher degrees of PEGylation may be formed depending upon the reaction conditions. PEGylated species can be separated from unconjugated IL-24 polypeptides using standard purification methods, such as dialysis, ultrafiltration, ion exchange chromatography, affinity chromatography, and the like.

PEGylation by alkylation generally involves reacting a terminal aldehyde derivative of PEG with IL-24 polypeptide in the presence of a reducing agent. PEG groups can be attached to the polypeptide via a —CH$_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of IL-24 polypeptide monopolymer conjugates.

Reductive alkylation to produce a substantially homogenous population of monopolymer IL-24 polypeptide conjugate molecule can comprise the steps of: (a) reacting a IL-24 polypeptide with a reactive PEG under-reductive alkylation conditions at a pH suitable to permit selective modification of the α-amino group at the amino terminus of the IL-24 polypeptide, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer IL-24 polypeptide conjugates, the reductive alkylation reaction conditions are those that permit the selective attachment of the water-soluble polymer moiety to the N-terminus of IL-24 polypeptide. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer: IL-24 polypeptide need not be as large because more reactive groups are available. Typically, the pH will fall within the range of 3 to 9, or 3 to 6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to IL-24 polypeptide will generally be in the range of 1:1 to 100:1. Typically, the molar ratio of water-soluble polymer to IL-24 polypeptide will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738, 846, Nieforth et al., *Clin. Pharmacol. Ther.* 59:636 (1996), Monkarsh et al., *Anal. Biochem.* 247:434 (1997)). This method can be employed for making IL-24 polypeptide-comprising homodimeric, heterodimeric or multimeric soluble receptor conjugates.

A pharmaceutical composition comprising IL-24 polypeptides can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

IL-24 polypeptides with IL-24 receptor binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconiugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified IL-24 polypeptides, for example IL-24 polypeptides linked with a polymer, as discussed above.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

IL-24 can also me administered in conjunction with other treatments for ovarian cancer such as surgery and chemotherapy. Examples of chemotherapeutic agents include but are not limited to paclitaxel, cisplatin, carboplatin, topotecan, hexamethylmelamine, ifosfamide, doxorubicin, bleomycin, Taxol, and etoposide.

Within one aspect, the present invention provides a method for inhibiting the growth and or proliferation of ovarian cancer cells comprising bringing IL-24 polypeptide into contact with the ovarian cancer cells in an amount sufficient to inhibit or reduce the proliferation of the ovarian cancer cells.

Within a second aspect, the present invention provides a method for treating a female mammal afflicted with ovarian cancer comprising administering to the female an isolated IL-24 polypeptide an amount of a composition of IL-24 polypeptide sufficient to inhibit or reduce the proliferation of the ovarian cancer. In one embodiment, the method is as described above, wherein the IL-24 polypeptide is administered in conjunction with radiation. In another embodiment, the method is as described above, wherein the IL-24 polypeptide is administered in conjunction with a chemotherapeutic agent. In another embodiment, the method is as described above, wherein the chemotherapeutic agent is selected from the group consisting of paclitaxel, cisplatin, carboplatin, topotecan, hexamethylmelamine, ifosfamide, doxorubicin, bleomycin, Taxol, and etoposide.

Within a third aspect, the present invention provides method for treating a female mammal afflicted with ovarian cancer comprising administering to the female an isolated IL-24 polypeptide an amount of a composition of IL-24 polypeptide sufficient to inhibit or reduce the proliferation of the ovarian cancer, and wherein the IL-24 polypeptide is fused with a cytotoxic moiety. In one embodiment, the method is as described above, wherein the cytotoxic moiety is a bacterial or plant toxin, cytotoxic radionuclide or cytotoxic drug.

Within another aspect, the present invention provides method of reducing proliferation of ovarian cancer cells comprising administering to a mammal with a ovarian neoplasm an amount of a composition of IL-24 polypeptide sufficient to reduce proliferation of the neoplastic ovarian cells. In one embodiment, the method is as described above, wherein the IL-24 polypeptide is administered in conjunction with radiation. In another embodiment, the method is as described above, wherein the IL-24 polypeptide is administered in conjunction with a chemotherapeutic agent. In another embodiment, the method is as described above, wherein the chemotherapeutic agent is selected from the group consisting of paclitaxel, cisplatin, carboplatin, topotecan, hexamethylmelamine, ifosfamide, doxorubicin, bleomycin, Taxol, and etoposide. In another embodiment, the method is as described above, wherein the IL-24 polypeptide is fused with a cytotoxic moiety. In another embodiment, the method is as described above, wherein the cytotoxic moiety is a bacterial or plant toxin, cytotoxic radionuclide or cytotoxic drug.

The invention is further illustrated by the following non-limiting examples.

EXAMPLE

We tested IL-24 in an Ovcar3 (ATCC #HTB-161) cytoxicity assay to measure the ability of IL-24 to prevent cells from growing during normal growth conditions. We used MTT reagent (Promega, Madison, USA) as our detection and readout for this cell inhibition assay. Procedure of a cytoxicity assay: Ovcar3 Cytotoxicity Assay Ovcar3 (ATCC #HTB-161) cells were plated at a density of 5000 cells/100ul/well in clear 96 well TC plates. Cells were plated in complete growth media consisting of RPMI containing 20% FBS, 0.01 mg/ml insulin, 2% HEPES, 1% Sodium Pyruvate and 1% Glutamax. Cells were incubated overnight at 37° C. in a 5% CO2 incubator.

The following day, media was removed from the cells and replaced with 100 ul/well of appropriately diluted samples. All sample dilutions were done in complete growth media. Samples were incubated on the cells for 72 hours.

After incubation, an MTT assay was done on the cells using the manufacturer's protocol (Promega #PAG4100). Dye solution was incubated on the cells 4 hours, followed by a 1 hour incubation with the stop solution. Absorbance was then read on the Victor II and percent inhibition was calculated from the wells containing complete growth media only.

Results

Retnoic Acid gave a 29% inhibition of growth at 3 uM, 34% at 10 uM, 43% at 31 uM, and 83% at 100 uM (positive control).

IL-24 gave a 4% inhibition of growth at 1 ng/ml, 9% at 10 ng/ml, 23% at 100 ng/ml and 52% at 1000 ng/ml.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for inhibiting the growth or proliferation of ovarian cancer cells in a mammal comprising bringing a soluble IL-24 polypeptide into contact with the ovarian cancer cells in an amount sufficient to inhibit or reduce the proliferation of the ovarian cancer cells, wherein said IL-24 polypeptide consists of amino acid residues 22 to 179 of SEQ ID NO:2, and wherein the IL-24 polypeptide is fused with a cytotoxic moiety selected from the group consisting of cytotoxic radionuclide or cytotoxic drug.

2. The method of claim 1, wherein the IL-24 polypeptide is administered in conjunction with radiation.

3. The method of claim 1, wherein the IL-24 polypeptide is administered in conjunction with a chemotherapeutic agent.

4. The method of claim 3, wherein the chemotherapeutic agent is selected from the group consisting of paclitaxel, cisplatin, carboplatin, topotecan, hexamethylmelamine, ifosfamide, doxorubicin, bleomycin, Taxol, and etoposide.

5. A method for inhibiting the growth or proliferation of ovarian cancer cells in a mammal comprising bringing a soluble IL-24 polypeptide into contact with the ovarian cancer cells in an amount sufficient to inhibit or reduce the proliferation of the ovarian cancer cells.

6. The method of claim 5, wherein the IL-24 polypeptide is fused with a cytotoxic moiety selected from the group consisting of cytotoxic radionuclide or cytotoxic drug.

7. The method of claim 5, wherein the IL-24 polypeptide is administered in conjunction with radiation.

8. The method of claim 5, wherein the IL-24 polypeptide is administered in conjunction with a chemotherapeutic agent.

9. The method of claim 8, wherein the chemotherapeutic agent is selected from the group consisting of paclitaxel, cisplatin, carboplatin, topotecan, hexamethylmelamine, ifosfamide, doxorubicin, bleomycin, Taxol, and etoposide.

* * * * *